US010321837B2

(12) United States Patent
Shilemay et al.

(10) Patent No.: US 10,321,837 B2
(45) Date of Patent: Jun. 18, 2019

(54) ECG MACHINE INCLUDING FILTER FOR FEATURE DETECTION

(71) Applicant: Biosense Webster (Israel) Ltd., Yokneam (IL)

(72) Inventors: Moshe Israel Shilemay, Haifa (IL); Yaron Ephrath, Karkur (IL); Oleg Khudish, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 7 days.

(21) Appl. No.: 15/582,156

(22) Filed: Apr. 28, 2017

(65) Prior Publication Data

US 2018/0310853 A1 Nov. 1, 2018

(51) Int. Cl.
*A61B 5/00* (2006.01)
*A61B 5/04* (2006.01)
(Continued)

(52) U.S. Cl.
CPC .......... *A61B 5/04017* (2013.01); *A61B 5/044* (2013.01); *A61B 5/0456* (2013.01);
(Continued)

(58) Field of Classification Search
CPC ........................ A61B 5/04017; A61B 5/04085
(Continued)

(56) References Cited

U.S. PATENT DOCUMENTS 5,503,160 A 4/1996 Pering et al.
5,521,851 A 5/1996 Wei et al.
(Continued)

FOREIGN PATENT DOCUMENTS

GB 2311676 A 10/1997

OTHER PUBLICATIONS

Sarita Mishra et al. “A Power-Line Interference Canceler Based on Sliding DFT Phase Locking Scheme for ECG Signals” IEEE Transactions on Instrumentation and Measurement, IEEE Service Center, Piscataway, NJ, US, vol. 64, No. 1, Jan. 2015.
(Continued)

*Primary Examiner* — Nadia A Mahmood
(74) *Attorney, Agent, or Firm* — Volpe and Koenig, P.C.

(57) ABSTRACT

A system and method of filtering input data to remove power line interference is disclosed. The system and method estimates the statistics of the input signal and include determining a value (R) from the ratio of a peak amplitude ($A_{peak}$) and a root-mean-square of the amplitudes of the interference harmonics ($A_{rms}$), calculate a running histogram of the determined value (R) to determine a threshold value ($TH_R$), comparing the determined value (R) to the determined threshold value ($TH_R$) to make a decision about feature existence, and outputting a feature decision. The system and method include estimating the interference level to determine if interference is low level or high level. The system and method include estimating interference using the feature detection, amplitude and phase; and removing the estimated interference from the signal to result in a signal substantially free of power line interference.

20 Claims, 16 Drawing Sheets

(51) Int. Cl.
*A61B 5/0408* (2006.01)
*A61B 5/0456* (2006.01)
*A61B 5/044* (2006.01)

(52) U.S. Cl.
CPC ........ *A61B 5/04085* (2013.01); *A61B 5/7203* (2013.01); *A61B 5/7221* (2013.01); *A61B 5/7246* (2013.01); *A61B 5/7264* (2013.01); *A61B 5/6823* (2013.01)

(58) Field of Classification Search
USPC .......................................................... 600/523
See application file for complete search history.

(56) References Cited

U.S. PATENT DOCUMENTS 5,738,104 A 4/1998 Lo et al.
6,351,664 B1 * 2/2002 Brodnick ........... A61B 5/04012 600/509
2014/0142894 A1 5/2014 Chang et al.
2016/0022164 A1 1/2016 Brockway et al.

OTHER PUBLICATIONS

B. Halder et al. "Detection and Identification of ECG waves by Histogram Approach" 2016 2nd International Conference on Control, Instrumentation, Energy & Communication (CIEC), IEEE, Jan. 28, 2016.
Maxime Yochum et al. "Automatic detection of P, QRS and T patterns in 12 leads ECG signal based on CWT" Biomedical Signal Processing and Control, Elsevier, Amsterdam, NL vol. 25, Nov. 28, 2015.
European Search Report dated Sep. 3, 2018 received in EP Application No. 18 16 9711.1.

* cited by examiner

ECG MACHINE INCLUDING FILTER FOR FEATURE DETECTION

SUMMARY

A system and method for performing an electrocardiograph (ECG) is disclosed. The system and method include a plurality of leads for attaching to a subject in order to capture electric signals, a signal processor to process the captured electrical signals by: applying a comb filter to the captured electrical signals to emphasize interference at a plurality of selected frequencies; estimating an amplitude and a phase of the applied filtered signals; performing a first stage of filtering the applied filtered signals to remove power line interference using feature detection; performing a second stage of filtering the applied filtered signals to remove power line interference using feature detection; estimating interference using the feature detection, amplitude and phase; and removing the estimated interference from the signal to generate a signal substantially free of power line interference, and an output device to output the process captured electrical signals.

BRIEF DESCRIPTION OF THE DRAWINGS

A more detailed understanding may be had from the following description, given by way of example in conjunction with the accompanying drawings wherein.

DETAILED DESCRIPTION

Figure 1:
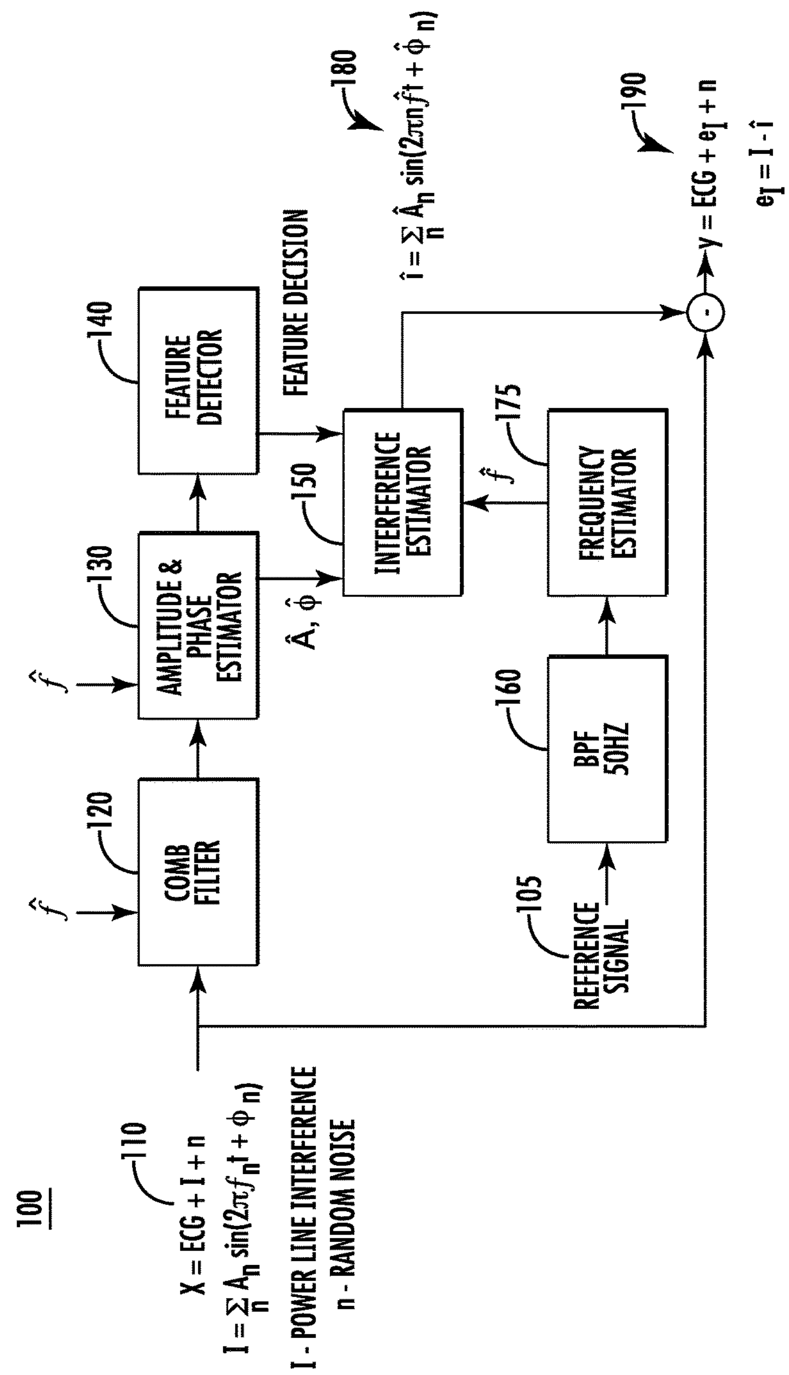
FIG. 1 illustrates a power line interference cancellation block diagram according to the present invention.

The present invention is related to electrocardiography. More particularly, the present invention is related to ECG filtering for feature detection. The process of electrocardiography performed by an electrocardiograph to produce an electrocardiogram, collectively referred to herein as ECG, and may also be referred to as EKG, receives interference from the AC power line. In order to understand and read the ECG, this interference is learned and often overestimated. When physicians use an ECG to study heart activity, an accounting for the interference needs to occur in order to isolate the electrical signals from the heart. This interference or noise, or other feature in the signal, is also referred to herein as a feature. Such features may also result from the processing of areas of the signal with sharp changes, peaks, and/or pacing signals including areas of high frequency and harmonics. Features obscure the accuracy of the ECG readings. Therefore, a need exists to provide improved methods of identifying features so that the effects of such features may be removed from the ECG study thereby allowing the electrical signals of the heart to be viewed.

Electrocardiography, referred to herein as ECG, and may also be referred to as EKG, is the process of recording the electrical activity of the heart over a period of time using electrodes placed on the skin, or inside the heart using a specialized catheter (i.e., intracardiac ECG). These electrodes detect the small electrical changes that arise from the heart muscle's electro-physiologic pattern of depolarizing during each heartbeat. ECGs are commonly or routinely performed cardiology tests. The machine used in the test is an electrocardiograph and the initial output is an electrocardiogram. For the sake of brevity, electrocardiography, electrocardiograph, and electrocardiogram are all referred to herein as ECG, and may also be referred to as EKG.

An intracardiac electrogram (ICEG) is an ECG with some added intracardiac leads (that is, inside the heart). Such an electrogram may be utilized in combination with, or in the alternative to, a conventional 12-lead ECG. In a conventional 12-lead ECG, 10 electrodes are placed on the patient's limbs and on the surface of the chest. The overall magnitude of the heart's electrical potential is then measured from 12 different angles ("leads") and is recorded over a period of time. A conventional 12-lead ECG may be performed over a period of time, such as 10 seconds, for example. In this way, the overall magnitude and direction of the electrical depolarization at the heart is captured at each moment throughout the cardiac cycle. A graph of voltage versus time produced by this medical procedure is referred to as an electrocardiogram. An ICEG may by recorded during an diagnostic or therapeutic procedure. The procedure duration may vary from tens of minutes to several hours. During each therapeutic procedure, usually there are several dozens of ablation sessions, each of which last several seconds up to approximately 1 minute, for example.

During each heartbeat, a healthy heart has an orderly progression of depolarization. This orderly pattern of depolarization gives rise to the characteristic ECG tracing. To the trained clinician, an ECG conveys a large amount of information about the structure of the heart and the function of its electrical conduction system. Among other things, an ECG can be used to measure the rate and rhythm of heartbeats, the size and position of the heart chambers, the presence of any damage to the muscle cells or conduction system of the heart, the effects of cardiac drugs, and the function of implanted pacemakers. Interpretation of the ECG is fundamentally about understanding the electrical conduction system of the heart. Normal conduction starts and propagates in a predictable pattern, and deviation from this pattern can be a normal variation or be pathological.

However, in order to ascertain the signals from the electrical conduction system of the heart, the measured signals need to be filtered to remove any unwanted and spurious signals or noise. Such spurious and unwanted signals may include, by example only, AC line noise.

FIG. 1 is a block diagram of a power line interference cancellation device 100. In its simplest form, power line interference cancellation device 100 inputs a signal, estimates the interference, and subtracts the estimated interference from the input signal to arrive at the signal of interest, the ECG.

An input signal 110 is provided to the power line interference cancellation device 100. Input signal 110 is illustrated as:

$$x=\text{ECG}+I+n \qquad \text{Equation 1}$$

where I is defined as the power line interference and n is random noise. The power line interference may be illustrated as:

$$I=\Sigma_n A_n \sin(2\pi f_n t+\varnothing_n) \qquad \text{Equation 2}$$

where $f_n$ is the fundamental interference frequency and associated harmonics, $A_n$ is the interference amplitude and $\phi_n$ is associated phase.

Power line interference cancellation device 100 depicts input signal 110 input into a comb filter 120. Generally, a comb filter adds a delayed version of a signal to itself, causing constructive and destructive interference. In this case, input signal 110 is input, along with an estimated frequency, $\hat{f}$, discussed herein with respect to frequency estimator 170, and then delayed and added to the input signal 110. The frequency response of comb filter 120 is a series of regularly spaced notches, giving the appearance of a comb. Comb filter 120 emphasizes the interference at specified frequencies and attenuates the spectral content of all other frequencies. In the depicted cancellation, the specified frequency may be set to 50 Hz and associated harmonics for systems operating where 50 Hz represents a predominate power line interference frequency, for example. As would be evident to one of ordinary skill in the art, when the predominate power line frequency is 50 Hz, harmonic frequencies of 50 Hz, such as 100 Hz, . . . , may also be common. Other power line frequencies include 60 Hz, for example, and the associated harmonic frequencies of 60 Hz, such as 120 Hz. Comb filter 120 provides for improved accuracy for non-integer number of samples in interference cycle, including those for frequencies other than 50 Hz or 60 Hz.

Comb filter 120 may be modified from common comb filters by calculating the residual effect of interference of a non-integer number of samples in an interference cycle. By denoting the sampling frequency by $f_s$, and the (fundamental) interference frequency by f, then when $$\frac{f_s}{f}\notin\mathbb{N},$$

where $\mathbb{N}$ denotes the set of natural numbers, the calculation may be less accurate, such as $$f_s = 4000\text{ Hz},\ f = 60\text{ Hz},\ \frac{f_s}{f} = 66\frac{2}{3}$$

samples per interference cycle, for example. This is the case in the previous algorithm (which in the above example performs the calculation for the first 66 samples, ignoring the ⅔ residual value). In the present algorithm, the non-integer residual value may be added to the calculations, leading to more accurate amplitude and phase estimation and overall lower residual noise after interference cancellation.

The output of the comb filter 120 is provided as an input into the amplitude and phase estimator 130, along with an estimated frequency, $\hat{f}$, discussed herein with respect to frequency estimator 170. Amplitude and phase estimator 130 estimates the amplitude, $\hat{A}$, and phase, $\hat{\varnothing}$, of the estimated interference output by comb filter 120. The amplitude, $\hat{A}$, and phase, $\hat{\varnothing}$, are then output to an interference estimator 150. Amplitude and phase estimator 130 provides improved accuracy for non-integer number of samples in the interference cycle. For each harmonic frequency, $f_n$, if the estimated frequency $\hat{f}_n=n\cdot\hat{f}_1$, where $\hat{f}_1$ is the estimated fundamental frequency, an estimate of the amplitude and phase may be calculated. This estimate may be performed as follows:

$$\int_0^{NT} x_{comb}\cdot\sin(2\pi\hat{f}_n t)dt \approx \int_0^{NT}[\Sigma_k A_k \sin(2\pi f_k t+\phi_k)]\cdot\sin(2\pi\hat{f}_n t)dt \approx \int_0^{NT} A_n \sin(2\pi f_n t+\phi_n)\cdot\sin(2\pi\hat{f}_n t)dt = \frac{A_n}{2}\int_0^{NT}\cos(4\pi f_n t+\phi_n)dt + \frac{A_n}{2}\cos(\phi_n)\int_0^{NT}dt = \frac{A_n}{2}\cos(\phi_n)\cdot NT \equiv S_1, \qquad \text{Equation 3}$$

where N is a natural number and $T=1/\hat{f}_1$—interference period. Since the comb filter emphasizes the interference harmonics and attenuates the other frequencies, as described herein above, Equation 3 represents a good approximation given that the sines and cosines with different frequencies are orthogonal, and may be equal to zero if the integral is performed over an integer number of cycles, repeating the process for $\int_0^{NT} x_{comb}\cdot\cos(2\pi\hat{f}_n t)dt$ provides $$\frac{A_n}{2}\sin(\phi_n)\cdot NT \equiv S_2,$$

where $$A_n = \sqrt{\left(\frac{2S_1}{NT}\right)^2+\left(\frac{2S_2}{NT}\right)^2} \text{ and } \phi_n = \tan^{-1}\frac{S_1}{S_2}.$$

In the discrete case, the integrals are replaced by sums over $N\cdot T\cdot f_s$ samples, which may be a non-integer number of samples. In the previous algorithm, sums were calculated using the integer part only—leading to inaccurate results (in the above derivation the integral is carried out over an integer number of cycles), while in the current algorithm the non-integer residual is considered.

The output of the amplitude and phase estimator 130 is also provided to a feature detector 140, which performs a threshold determination as will be discussed herein below to make a feature decision that is then output to the interference estimator 150. Feature detector 140 provides an interference amplitude level estimation and applies different feature detection mechanisms for low and high interference levels instead of the previous mechanism for all interference levels. Feature detector 140 may apply an adaptive threshold (TH) using two running histograms, including pre- and post-filtered signals, as compared to the previously used constant TH in previous algorithms, as constant TH fails or falters at higher interference levels. TH may be calculated by setting a wanted or desired percentage level of the cumulative distribution function (CDF) calculated from the histogram, as will be described in more detail below.

In this method, the first histogram can be thought of as an interference level normalization stage, in which most of the high level interference is estimated and subtracted, at the expense of moderate feature detection capability. The feature detection confidence is than increased by the second histogram/filtering stage. Feature detector 140 provides better signal treatment in consecutive feature detections, for example.

Power line interference cancellation device 100 may include a reference signal 105 input into a bandpass filter (BPF) 160. Reference signal 105 may take the form of $Ref=n+\Sigma_k A_k \sin(2\pi f_k t+\O_k)$. A digital BPF is a computational algorithm that passes frequencies within a certain range and rejects (attenuates) frequencies outside that range. In power line interference cancellation device 100, BPF 160 may be configured to operate at 50 Hz for systems operating where 50 Hz represents a predominate power line interference frequency, for example. Other power line interference frequencies include 60 Hz, for example, and these may be used in bandpass filter 160 as appropriate.

The output of bandpass filter 160 may be input to a frequency estimator 170. Frequency estimator 170 may output a frequency, $\hat{f}$, which will be used as input to interference estimator 150. Since the noise corrupting the reference signal is assumed to have zero mean, using a longer time period for frequency estimation is equivalent to averaging more of the noise, leading the result closer to the assumed zero mean.

Interference estimator 150 may combine the input amplitude, $\hat{A}$, and phase, $\hat{\O}$, from amplitude and phase estimator 130 and frequency, $\hat{f}$, from frequency estimator 170 to estimate the interference 180. Based on the inputs discussed herein, the interference 180 may be illustrated as:

$$\hat{I}=\Sigma_n \hat{A}_n \sin(2\pi n\hat{f}t+\hat{\O}_n) \quad \text{Equation 4}$$

where n indicates the nth harmonic of the interference signal.

The estimated interference 180 (Equation 4) is then subtracted from the input signal 110 (Equation 1) to produce an output signal 190. Output signal 190 may illustrated as:

$$y=ECG+e_I+n \quad \text{Equation 5}$$

where $e_I=I-\hat{I}$ is the interference estimation error, with I defined by Equation 2 and $\hat{I}$ defined by Equation 4.

The importance of the interference estimator 150 is evident in that any error, either over-estimating or under-estimating the interference, results in an effect on the output signal 190. For example, the closer the interference (Equation 2) is represented by interference 180 (Equation 4), the more precise and accurate the output signal 190 describes the true electric behavior of the heart. If I defined by Equation 2 and $\hat{I}$ defined by Equation 4 are more accurately matched (better estimating of interference), $e_I$ becomes smaller and output signal 190 defined by Equation 5 approximates ECG plus random noise.

Feature detector 140 may operate using a constant threshold, for example. In such operation, each ECG channel may be checked by the feature detector 140 to determine if a feature exists in the data, and if so, the data is not used. The ECG signals are detected by the body surface leads as well as by the intracardiac electrodes. In general, each of these channels may be corrupted by a different amount of interference. The interference may be different at different times and places, including different operating rooms, time of day, etc., for example. Constant thresholding cannot be optimized to appropriately accommodate at all channels in all places and times, and an adaptive, learning mechanism may be utilized.

A constant threshold may be illustrated as:

$$A_{peak}>TH\cdot A_{rms}+n_{min} \quad \text{Equation 6}$$

where $A_{peak}=0.5*(A_{max}-A_{min})$, $A_{rms}=\sqrt{\Sigma A_n^2}$ calculated for each data packet (50 ms), and TH=constant threshold, such as 1.25, for example. The terminology $A_{max}$ and $A_{min}$ refers to the minimum and maximum values of the current data packet as output from the comb filter. The use of a constant threshold in feature detector 140 may provide poor performance at high levels of interference, such as several milli-Volt (mV) and above.

Feature detector 140 may operate using an adaptive threshold in order to overcome the poor performance of the constant threshold at high levels of interference and variance in different channels, places and times. The adaptive threshold may employ a first histogram process and a second histogram process as described below.

Figure 2:
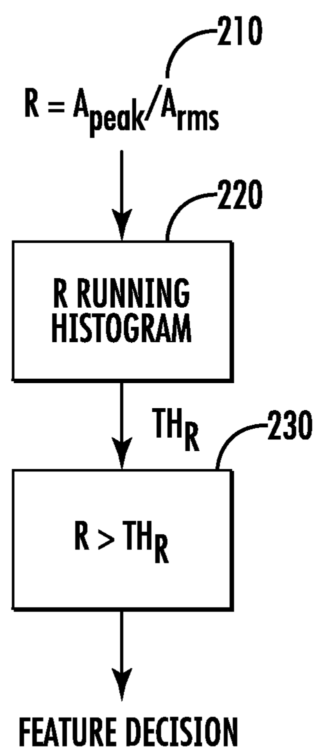
FIG. 2 illustrates the first histogram process.

FIG. 2 illustrates the first histogram process 200. The first histogram process 200 includes a dynamic histogram of R, where $R=A_{peak}/A_{rms}$ at step 210. At step 220, R is included in a running histogram to determine $TH_R$. A running histogram of R is calculated using the last $N_R$ where:

$$Hist_R=f(R_{n-N_{R+1}},R_{n-N_{R+2}}, \ldots ,R_n) \quad \text{Equation 7}$$

A cumulative distribution function (CDF) is calculated according to:

$$CDF_R=f(Hist_R) \quad \text{Equation 8}$$

The adaptive threshold may be calculated based on the CDF where:

$$TH_R=f(CDF_R) \quad \text{Equation 9}$$

using $TH_R$ in step 230, it is determined if $R>TH_R$ resulting in the feature decision of feature detector 140 of FIG. 1.

Figure 3:
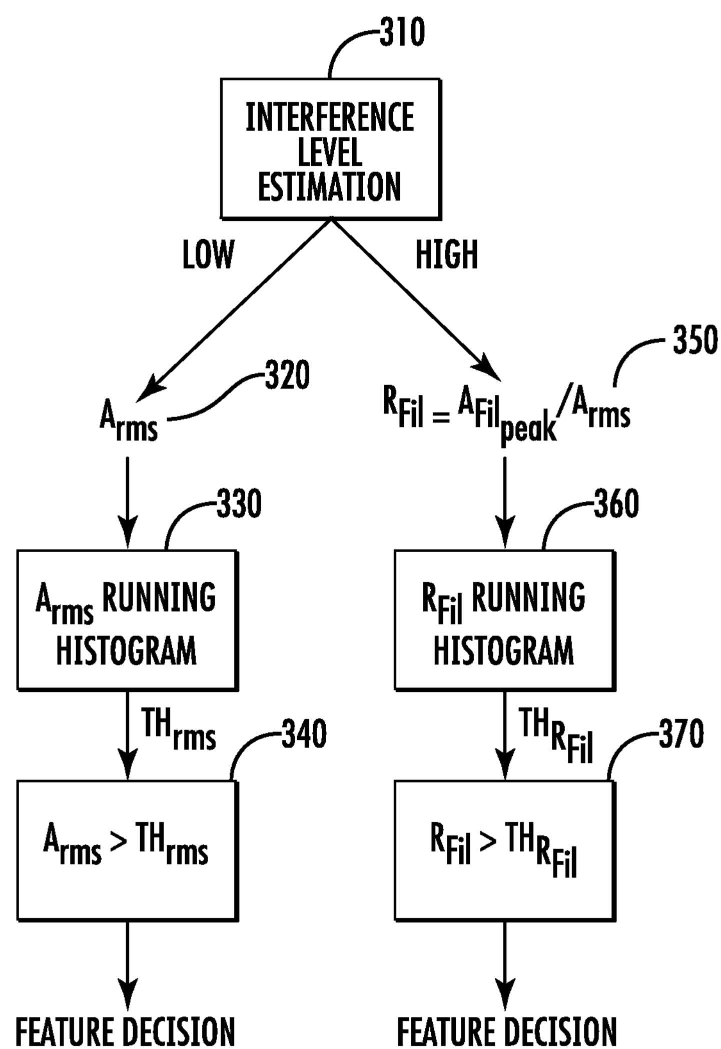
FIG. 3 illustrates the second histogram process.

FIG. 3 illustrates the second histogram process 300. The second histogram process 300 includes performing an interference level estimate at step 310. If the estimate 310 of interference level is low, then $A_{rms}$ is calculated at step 320. A low level of interference is a predefined or predetermined level, such as approximately 200 µV or less, for example. Low level interference is further discussed in FIGS. 9-12 below. At step 330, $A_{rms}$ is included in a running histogram to determine $TH_{rms}$. The running histogram is calculated in a similar manner to Equations 7-9, with the necessary changes. Using $TH_{rms}$ in step 340, it is determined if $A_{rms}>TH_{rms}$ resulting in the feature decision of feature detector 140 of FIG. 1.

If the estimate 310 of interference level is high, then $R_{Fil}=A_{Fil_{peak}}/A_{rms}$ is calculated at step 350, where $A_{Fil_{peak}}$ is the peak amplitude (half the difference of maximum and minimum value) of the signal which was filtered in the first filtering stage (according to the first histogram feature decision). A high level of interference is a predefined or predetermined level, such as approximately interference in range of 3000 to 13000 μV or more, for example. High level interference is further discussed in FIGS. 5-8 below. At step 360, $R_{Fil}$ is included in a running histogram to determine $TH_{R_{Fil}}$ as set forth above in Equations 7-9, with the necessary changes. Using $TH_{R_{Fil}}$ in step 370, it is determined if $R_{Fil}>TH_{R_{Fil}}$ resulting in the feature decision of feature detector 140 of FIG. 1.

Figure 4:
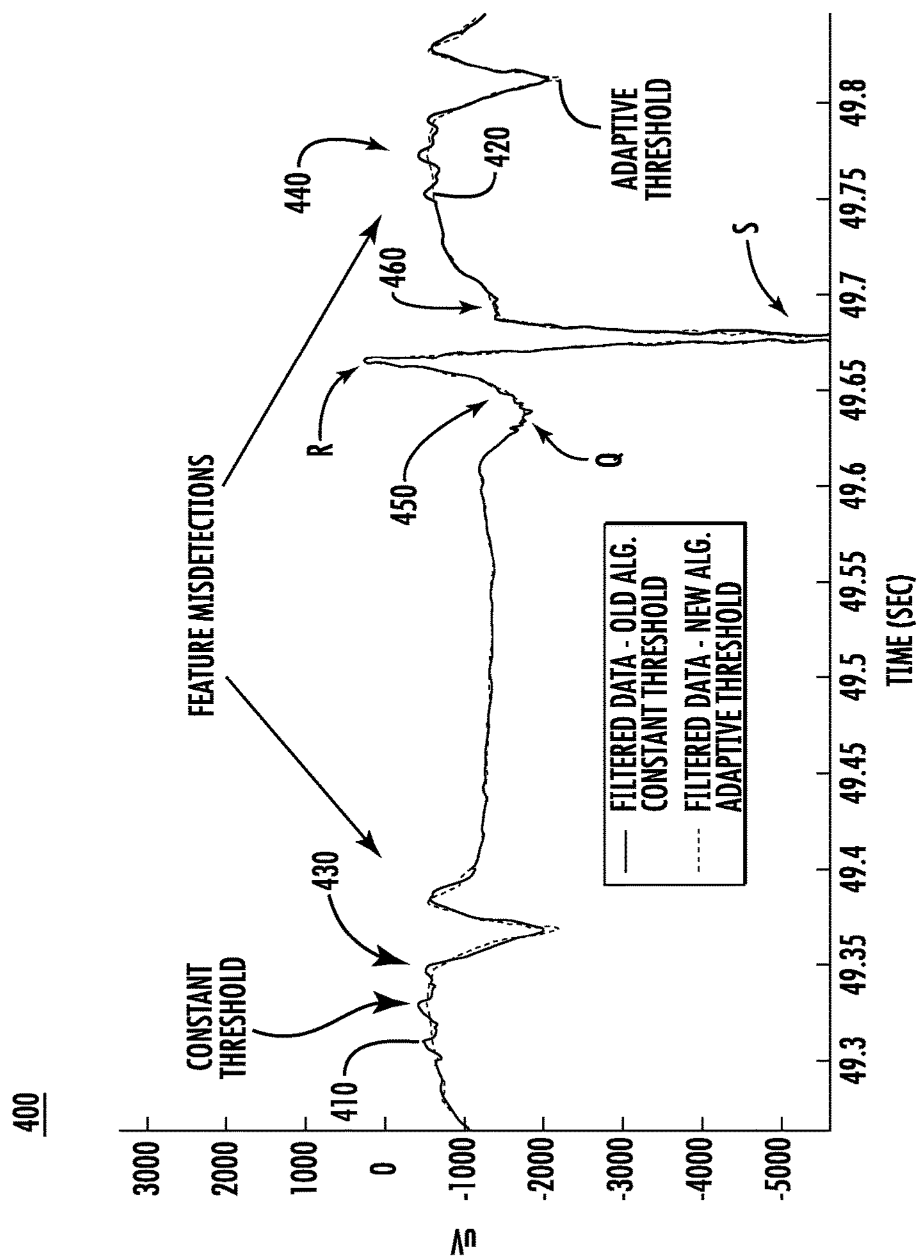
FIG. 4 illustrates ECG plots for filtered data using a constant threshold and for filtered data using an adaptive threshold.

FIG. 4 illustrates ECG plots 400 for filtered data using a constant threshold 410 and for filtered data using an adaptive threshold 420. The plots are provided as μV vs. time (sec). As shown in the plots 400, the filtered data using a constant threshold 410 includes feature misdetections 430, 440 not evident in the filtered data using an adaptive threshold 420. For example, feature misdetections 430 are evident during times between 49.3 and 49.35 seconds. Feature misdetections 430 may be approximately 200 μV in amplitude. By way of an additional example, feature misdetections 440 are evident during times between 49.75 and 49.8 seconds. Feature misdetections 440 may be approximately 200 μV in amplitude. In FIG. 4 there are also small ripples 450, 460 on either side of the QRS complex (labeled Q, R, S), which do not appear when using adaptive threshold.

Figure 5:
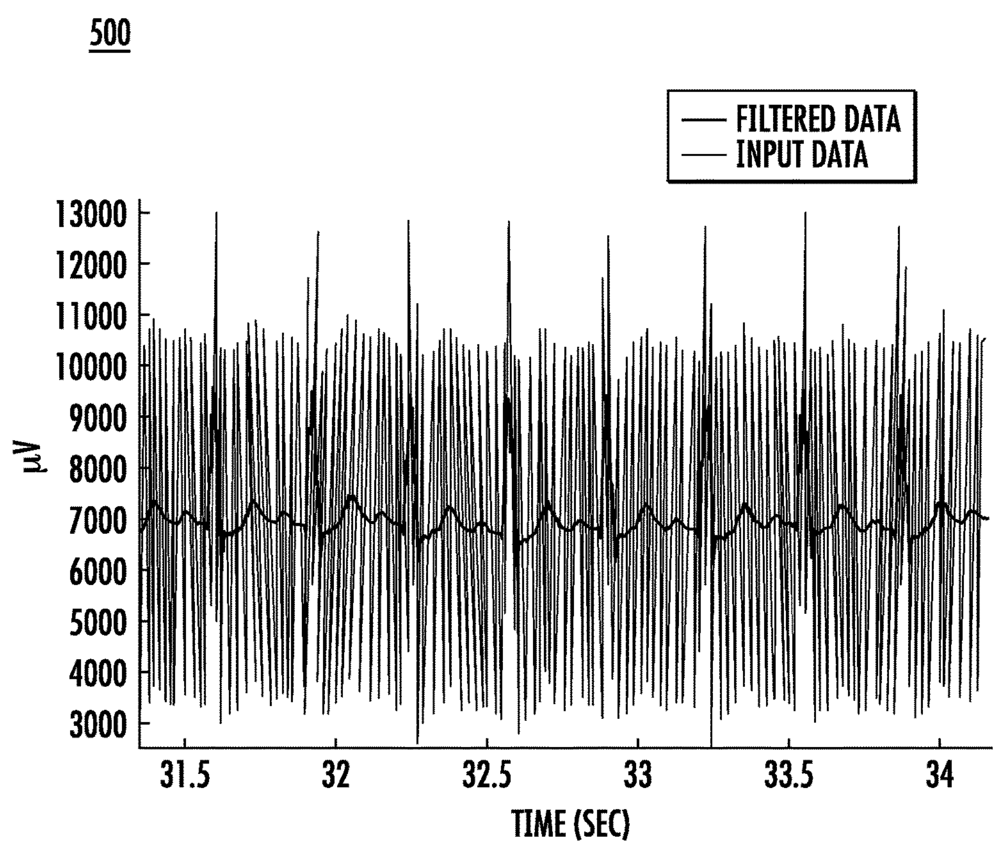
FIG. 5 illustrates a high interference level example depicting filtered data using an adaptive threshold and input data.

FIG. 5 illustrates a high interference level example 500 depicting filtered data using an adaptive threshold and input data. The filtered data is generated from the input data using a high interference level adaptive threshold described herein. This plot illustrates that the filtered data signal successfully rejected the high level interference.

Figure 6:
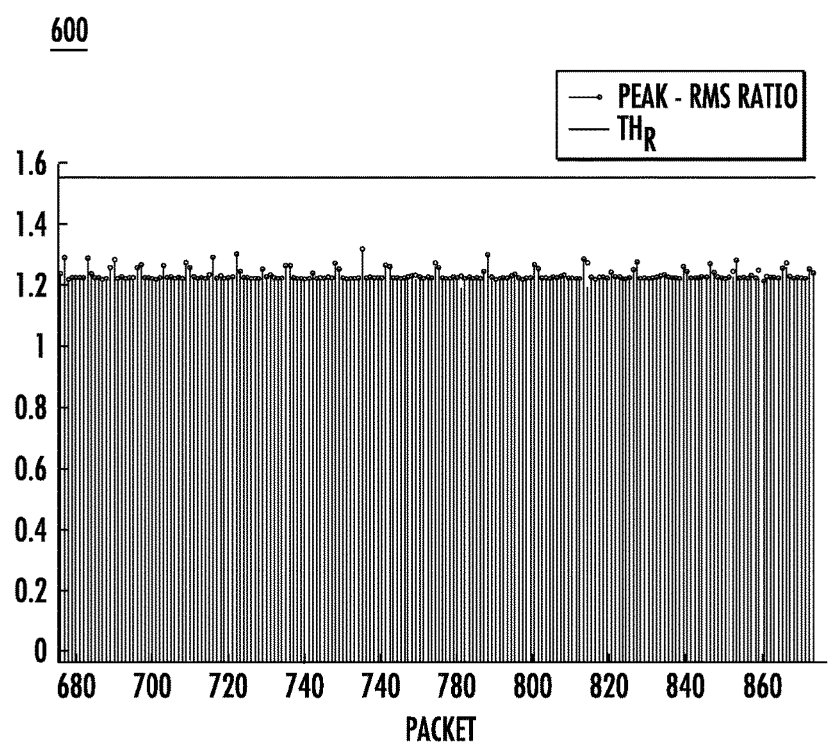
FIG. 6 illustrates a high interference level example depicting the first histogram buffer, Peak-RMS Ratio buffer, and its corresponding adaptive threshold, $TH_R$.

FIG. 6 illustrates a high interference level example 600 depicting the first histogram buffer, i.e., Peak-RMS Ratio buffer, and its corresponding adaptive threshold, $TH_R$. The adaptive threshold $TH_R$ represents the first histogram calculated from the Peak-RMS Ratio buffer. This plot of the high interference level example 600 illustrates that a feature is detected when Peak-RMS Ratio value exceeds $TH_R$. However, in the presence of high level interference this mechanism fails to detect features, and illustrates the need for a second mechanism.

Figure 7:
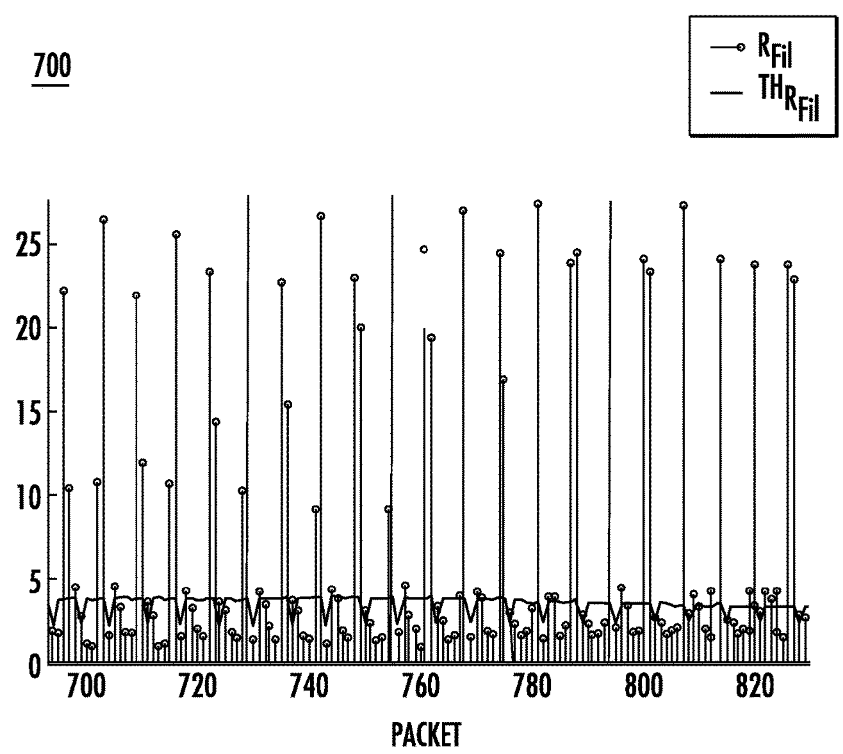
FIG. 7 illustrates a high interference level example depicting the second histogram buffer, $R_{Fil}$, and $TH_{R_{Fil}}$.

FIG. 7 illustrates a high interference level example 700 depicting the second histogram buffer, i.e. $R_{Fil}$ buffer, and $TH_{R_{Fil}}$. The adaptive threshold $TH_{R_{Fil}}$ represents the second histogram calculated from the $R_{Fil}$ buffer in high interference situations. This plot of the high interference level example 700 illustrates that a feature is detected when $R_{Fil}$ exceeds $TH_{R_{Fil}}$. It can be seen from FIG. 7 that the first filtering stage (first histogram) 'normalized' the interference level, allowing the second filtering stage to detect features in the presence of high level interference.

Figure 8:
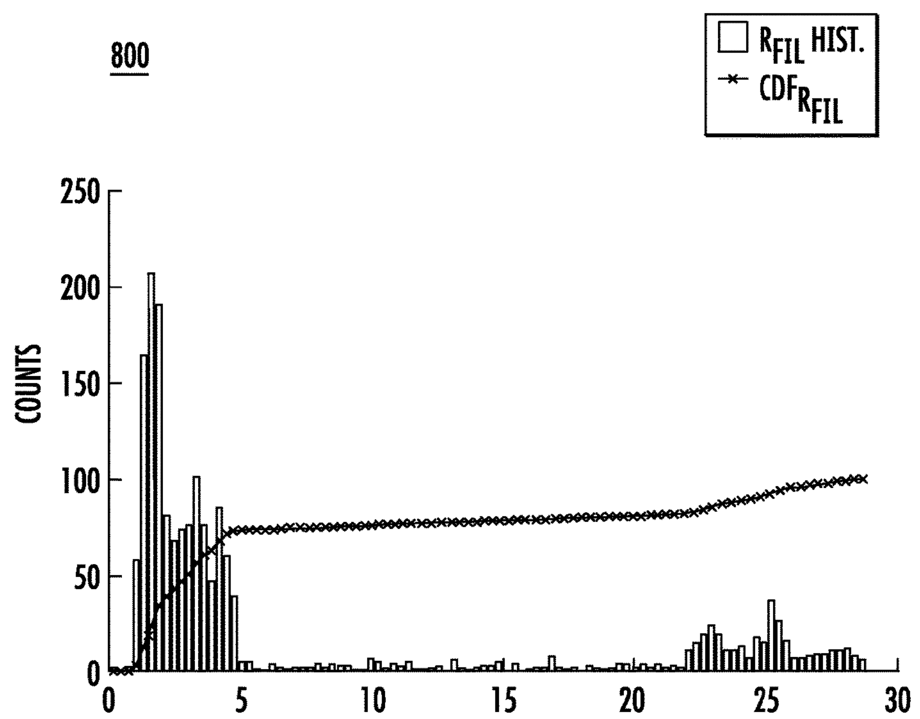
FIG. 8 illustrates a high interference level example depicting the second histogram $R_{Fil}$Hist and its corresponding cumulative distribution function (CDF) $CDF_{R_{Fil}}$.

FIG. 8 illustrates a high interference level example 800 depicting $R_{Fil}$Hist and $CDF_{R_{Fil}}$—the second histogram. This plot of the high interference level example 800 illustrates the histogram generated using an $R_{Fil}$ buffer, and its corresponding calculated CDF. It can be seen from FIG. 8 that there are two main clusters of values: a large cluster approximately from values 1 to 5, and a smaller cluster approximately from values 23 to 28. These two clusters approximately represent areas without and with features, respectively.

Figure 9:
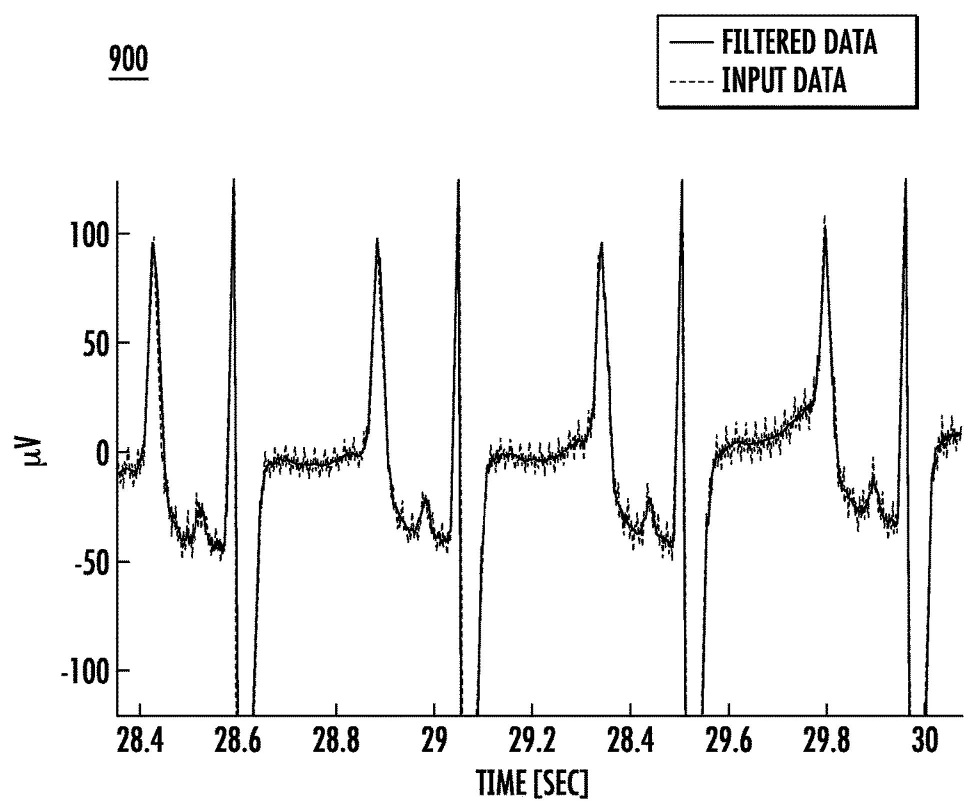
FIG. 9 illustrates a low interference level example depicting filtered data using an adaptive threshold and input data.

FIG. 9 illustrates a low interference level example 900 depicting filtered data using an adaptive threshold and input data. The filtered data is generated from the input data using a low interference level adaptive threshold described herein.

Figure 10:
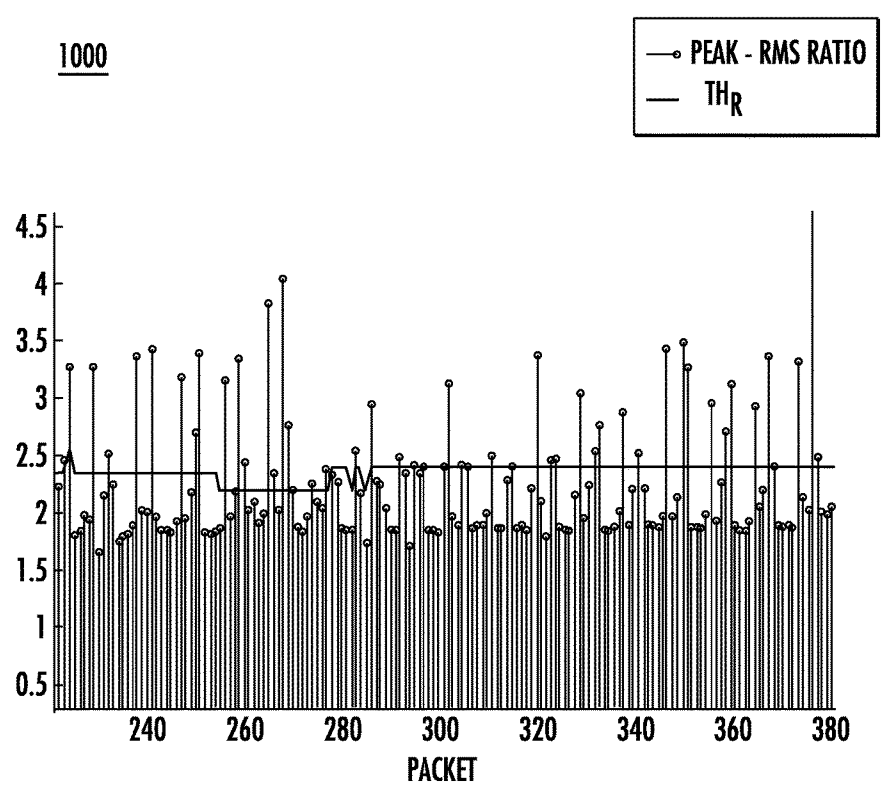
FIG. 10 illustrates a low interference level example depicting the first histogram buffer, Peak-RMS Ratio buffer, and its corresponding adaptive threshold, $TH_R$.

FIG. 10 illustrates a low interference level example 1000 depicting the first histogram buffer, i.e. Peak-RMS Ratio buffer, and its corresponding adaptive threshold, $TH_R$. This plot of the low interference level example 1000 illustrates that for low level interference this mechanism is detecting features. Nevertheless the detection is not optimal and some features can be missed.

Figure 11:
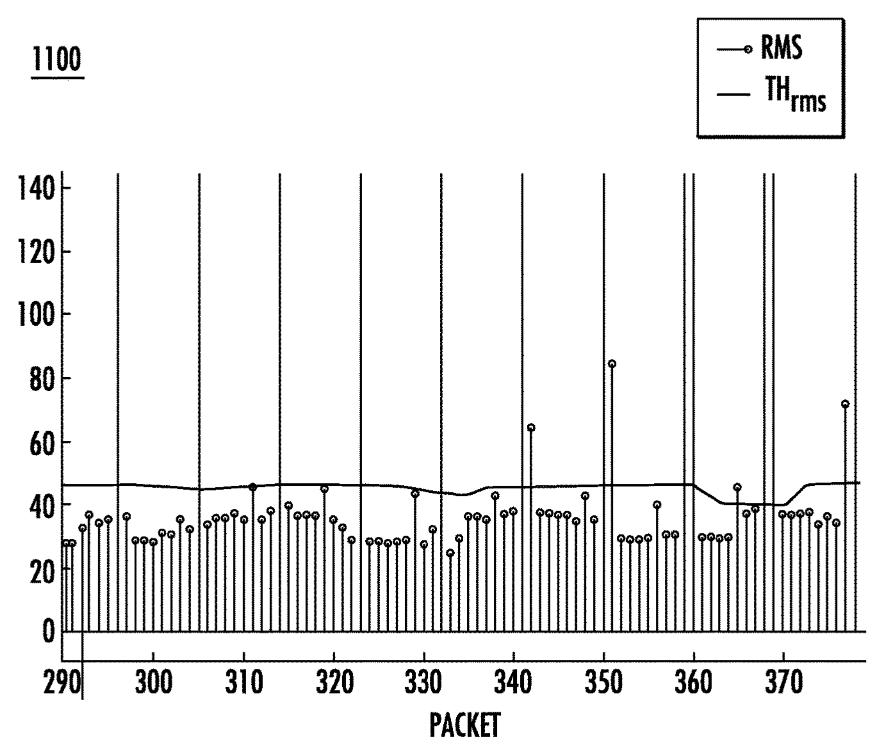
FIG. 11 illustrates a low interference level example depicting RMS and $TH_{rms}$.

FIG. 11 illustrates a low interference level example 1100 depicting RMS buffer and its corresponding $TH_{rms}$. The adaptive threshold $TH_{rms}$ is calculated from the second histogram calculated from the RMS buffer in low interference situations. This plot of the low interference level example 1100 illustrates that the first filtering stage (first histogram) 'normalized' the interference level, allowing the second filtering stage to better distinguish features from its surroundings, as can be seen from the higher dynamic range—here features are more than 7 times higher than other regions (larger than 140 compared to 20), where in the first histogram this ratio was less than 2 (4 compared to 2).

Figure 12:
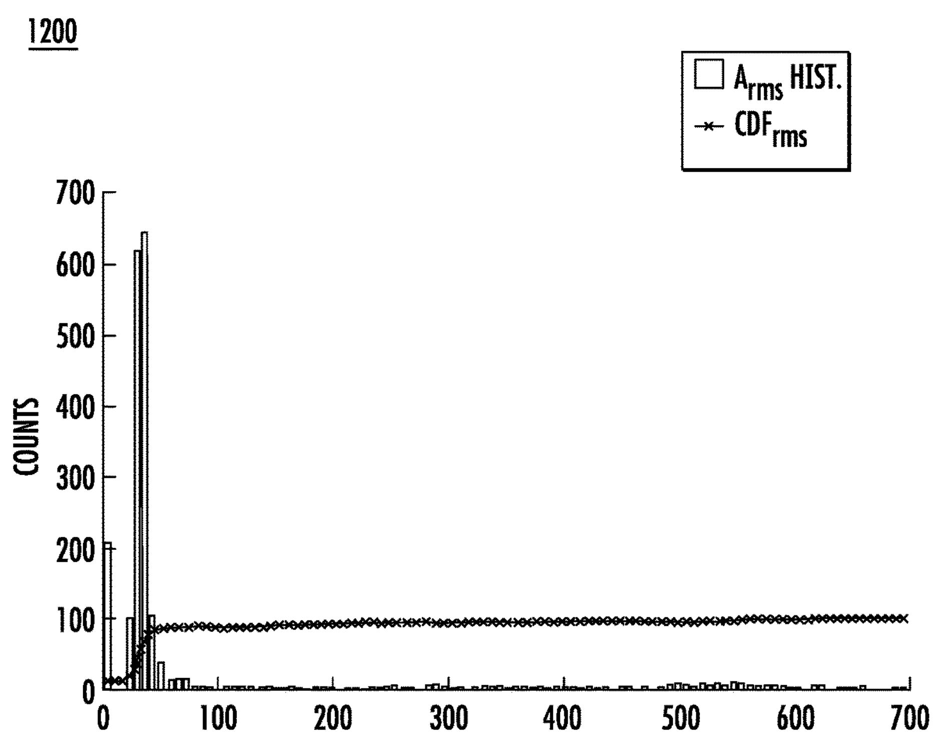
FIG. 12 illustrates a low interference level example depicting the second histogram $A_{rms}$Hist and its corresponding CDF $CDF_{RMS}$.

FIG. 12 illustrates a low interference level example 1200 depicting the second histogram $A_{rms}$Hist and its corresponding CDF $CDF_{RMS}$. This plot of the low interference level example 1200 illustrates the histogram generated using $A_{rms}$Hist buffer, and its corresponding calculated CDF.

Figure 13:
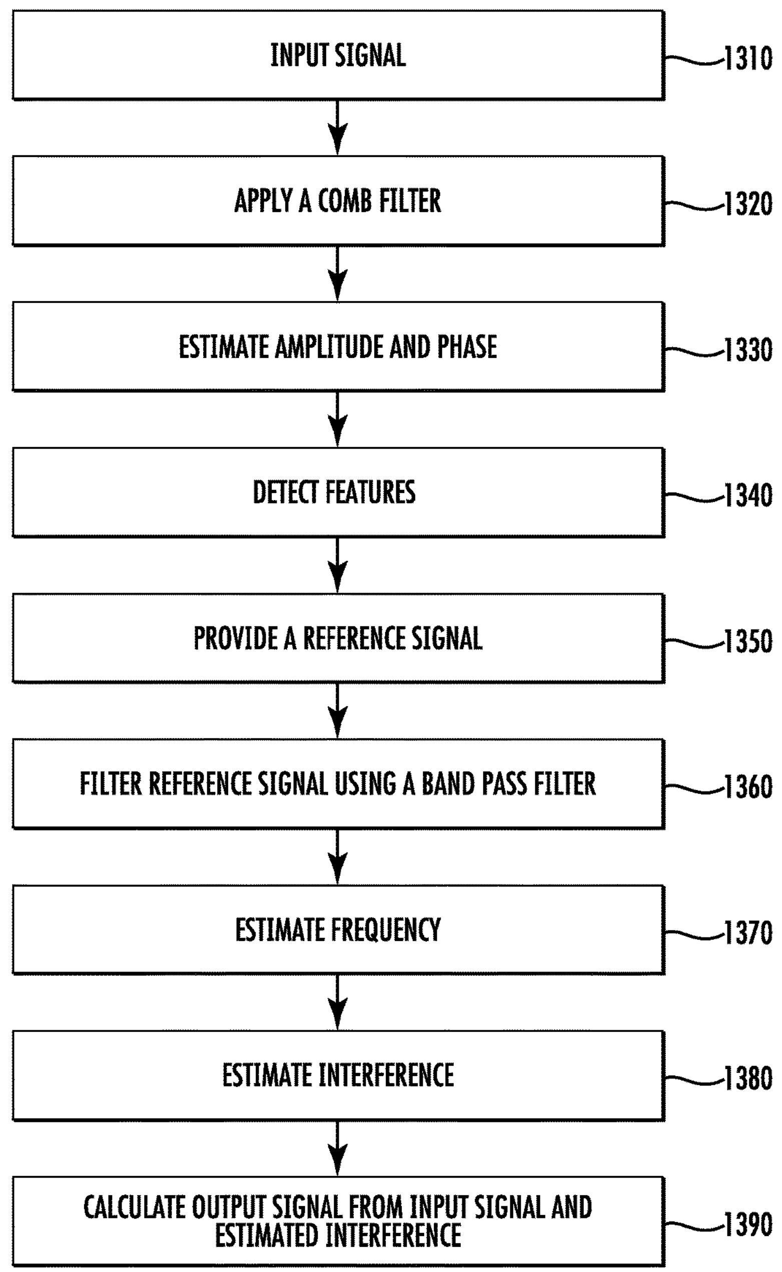
FIG. 13 illustrates a method of performing power line interference cancellation.

FIG. 13 illustrates a method 1300 of performing power line interference cancellation. Method 1300 may be performed by the device 100 of FIG. 1. Method 1300 includes inputting a signal from an ECG system at step 1310. At step 1320, method 1300 applies a comb filter to the input signal. At step 1330, the amplitude and phase are estimated from the filtered input signal to produce amplitude and phase. At step 1340, features are detected and a feature decision is provided.

Method 1300 provides a reference signal at step 1350. At step 1360, the reference signal is filtered using a band pass filter. At step 1370, the frequency of the band pass filtered reference signal is estimated.

At step 1380, the interference is estimated using the estimated amplitude and phase, the feature decision and the estimated frequency. The output signal is calculated from the input signal and the estimated interference, at step 1390.

While FIG. 13 implies that the frequency estimation is sequential to the amplitude and phase estimation, these estimations may be executed in parallel. Specifically, the frequency estimation may be carried out in intervals of about 60 seconds, i.e., every 60 seconds the frequency is estimated, as is described in steps 1350-1370. After the first frequency estimation, amplitude and phase is estimated every 50 ms for each ECG channel separately as is described in steps 1310-1340 and 1380-1390.

Figure 14:
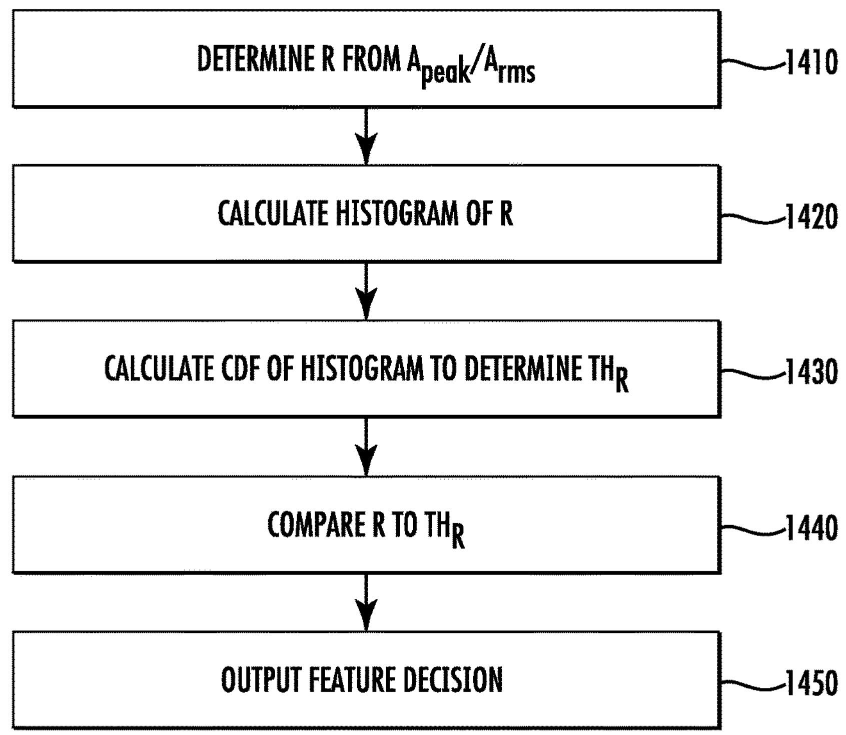
FIG. 14 illustrates a method of performing feature detection using an adaptive threshold for a first histogram.

FIG. 14 illustrates a method 1400 of performing feature detection using an adaptive threshold for a first histogram. Method 1400 includes determining R from $A_{peak}/A_{rms}$ at step 1410. At step 1420, a histogram of R may be calculated. After the histogram is updated, its CDF is calculated, and $TH_R$ is determined according to this CDF at step 1430. The independent parameter (x axis) of the CDF are R values, and the dependent variable (y axis) is the cumulative prevalence up to this R value (in percentage) as shown in FIG. 8, for example. In order to calculate $TH_R$, a desired percentage level may be established, such as 65%, for example, and search where the CDF first exceeds this level. The corresponding R value is $TH_R$. The R values are learned during the last time interval, such as 5 seconds, for example and choose appropriate TH accordingly. The threshold of the other histograms may be calculated in a similar manner. At step 1440, R is compared to $TH_R$. At step 1450, a feature decision is output to an interference estimator.

Figure 15:
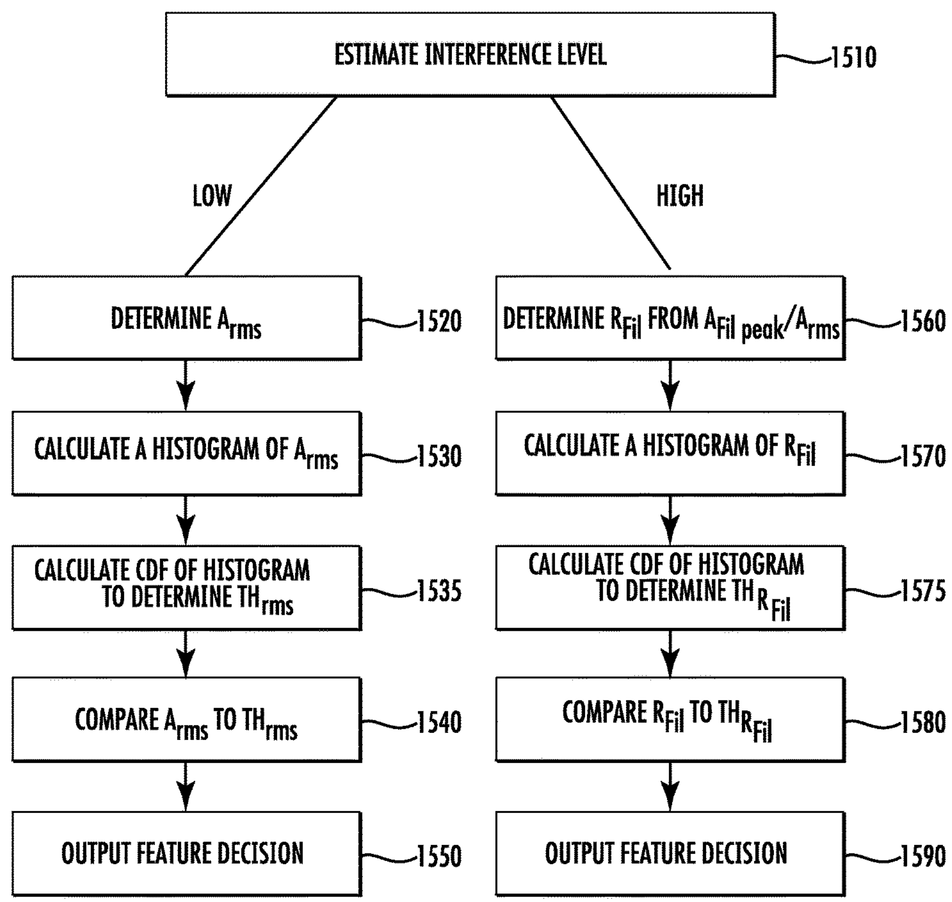
FIG. 15 illustrates a method of performing feature detection using an adaptive threshold for a second histogram.

FIG. 15 illustrates a method 1500 of performing feature detection using an adaptive threshold for a second histogram. Method 1500 includes an estimate of the interference level at step 1510.

If the estimate of the interference level is low, then $A_{rms}$ is determined at step 1520. At step 1530, a histogram of $A_{rms}$ is calculated and its CDF calculated at step 1535 to determine $TH_{rms}$. Using $TH_{rms}$ in step 1540, $A_{rms}$ is compared to $TH_{rms}$ to output a feature decision at step 1550.

If the estimate of the interference level is high, the $R_{Fil}$ is determined from $A_{peak}/A_{rms}$ at step 1560. At step 1570, a histogram of $R_{Fil}$ is calculated and its CDF is calculated at step 1575 to determine $TH_{R_{Fil}}$. Using $TH_{R_{Fil}}$ in step 1580, $R_{Fil}$ is compared to $TH_{R_{Fil}}$ to output a feature decision at step 1590.

Figure 16:
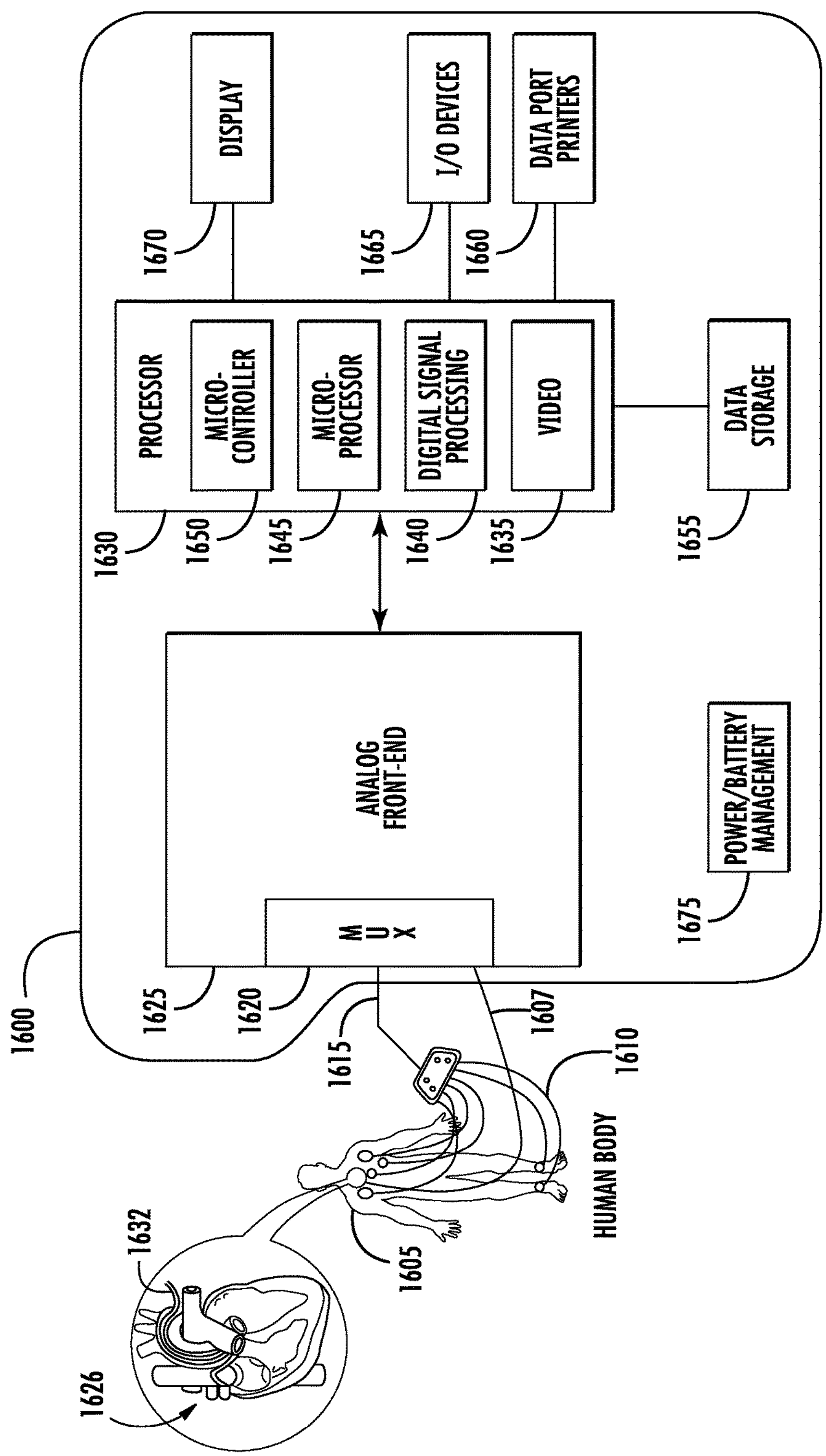
FIG. 16 illustrates a block diagram of an ECG.

FIG. 16 illustrates a block diagram of a device 1600 in which the power line interference cancellation device 100 is utilized. Device 1600 may take the form of an ECG machine. Device 1600 includes a series of leads 1610 that taper into a single multiplexed input 1615. The series of leads 1610 may be placed on a human test subject 1605. Additional leads 1607, which may be included with series of leads 1610, or separate therefrom (as shown) may be intracardiac leads 1607.

Intracardiac leads 1607 may be used for diagnostic or therapeutic treatment, such as for mapping electrical potentials in a heart 1626 of a patient 1605. Alternatively, intracardiac leads 1607 may be used, mutatis mutandis, for other therapeutic and/or diagnostic purposes in the heart or in other body organs.

Intracardiac leads 1607 may be inserted in the vascular system of the patient 1605 so that a distal end 1632 of the leads 1607 enters a chamber of the patient's heart 1626. Although FIG. 16 shows a single lead 1607 with a single location sensor, embodiments of the present invention may utilize probes with more than one location sensor.

The signals on the series of leads 1610 are input into an analog front-end 1625 via an input multiplexor 1620. The analog front-end 1625 provides to, and is controlled by, a processor 1630. Processor 1630 may include, as shown, a video controller 1635, digital signal processor 1640, a microprocessor 1645, and a micro controller 1650. Processor 1630 is coupled to a data storage 1655. Data ports and printers 1660 may be coupled to processor 1630. Other input/output devices 1665 may be coupled to processor 1630 including a printer to provide hard copy outputs of ECGs. A display 1670 may be used to provide output of the signals of the ECG to a doctor or other medical personnel. A power/battery management system 1675 may be included to provide power for device 1600 to operate.

Series of leads 1610 includes both the generally used forms of electrodes and leads. The series of leads 1610 may include a conductive pad in contact with the body 1605 that makes an electrical circuit with the electrocardiograph. On a standard 12-lead ECG there are only 10 leads 1610. Series of leads 1610 may be grouped into three sets: limb, augmented limb, and precordial. Generally, the 12-lead ECG has a total of three limb leads and three augmented limb leads arranged like spokes of a wheel in the coronal plane (vertical) and six precordial leads that lie on the perpendicular transverse plane (horizontal).

Analog front-end 1625 receives the signals from the series of leads 1610 and performs analog processing, such as filtering, of the signals.

Data storage 1655 is any device that records information. Data storage may provide a storage medium for the signals includes within device 1600 and a place for calculations of processor 1630 to be stored.

Microprocessor 1645 may be a computer processor which incorporates the functions of a computer's central processing unit (CPU) on a single integrated circuit (IC), or a few integrated circuits. Microprocessor 1645 may be a multipurpose, clock driven, register based, programmable electronic device which accepts digital or binary data as input, processes it according to instructions stored in its memory or data storage 1655, and provides results as output. Microprocessor 1645 contains both combinational logic and sequential digital logic.

Micro controller 1650 may be one or more small computers on a single integrated circuit. Micro controller 1650 may contain one or more CPUs along with memory and programmable input/output peripherals. Program memory in the form of Ferroelectric RAM, NOR flash or OTP ROM is also often included on chip, as well as a small amount of RAM. Microcontrollers are designed for embedded applications, in contrast to the microprocessors used in personal computers or other general purpose applications consisting of various discrete chips.

Digital signal processor 1640 may perform digital signal processing to perform a wide variety of signal processing operations. The signals processed in this manner are a sequence of numbers that represent samples of a continuous variable in a domain such as time, space, or frequency. Digital signal processing can involve linear or nonlinear operations. Nonlinear signal processing is closely related to nonlinear system identification and can be implemented in the time, frequency, and spatio-temporal domains. The application of digital computation to signal processing allows for many advantages over analog processing in many applications, such as error detection and correction in transmission as well as data compression. DSP is applicable to both streaming data and static (stored) data.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A system for performing an electrocardiograph (ECG), the system comprising:
- a plurality of leads for attaching to a subject in order to capture electric signals;
- a signal processor to process the captured electrical signals by:
  - applying a comb filter to the captured electrical signals to emphasize interference at a plurality of selected frequencies;
  - estimating an amplitude and a phase of the applied filtered signals;
  - performing a first stage of filtering the applied filtered signals to remove power line interference using feature detection;
  - performing a second stage of filtering the applied filtered signals to remove power line interference using feature detection, the second stage including estimating the interference level to determine if interference is low level or high level;
  - estimating interference using the feature detection, amplitude and phase; and
  - removing the estimated interference from the signal to generate a signal substantially free of power line interference; and
- an output device to output the process captured electrical signals.

2. The system of claim 1 wherein the first stage comprises:
- determining a first value (R) from a ratio of a peak amplitude ($A_{peak}$) and a root-mean-square of the amplitude ($A_{rms}$);
- calculating a running a histogram of the determined first values (R) to estimate a plurality of signal statistics and determine a threshold value ($TH_R$) accordingly;
- comparing the determined value (R) to the determined threshold value ($TH_R$); and
- outputting an feature decision based on the comparison.

3. The system of claim 1 further comprising, on a condition that there is low level interference in the estimate:
- determine a root-mean-square of the amplitudes of the interference harmonics ($A_{rms}$);
- calculate a running histogram of the determined root-mean-square of the amplitude ($A_{rms}$) to determine a threshold value ($TH_{rms}$);
- compare the root-mean-square of the amplitude ($A_{rms}$) to the determined threshold value ($TH_{rms}$); and
- outputting an feature decision based on the comparison.

4. The system of claim 1 further comprising, on a condition that there is high level interference in the estimate:
- determine a first value ($R_{Fil}$) from a ratio of (first stage) filtered signal peak amplitude ($A_{Filpeak}$) and a root-mean-square of the amplitude ($A_{rms}$);
- calculate a running histogram of the values ($R_{Fil}$) to determine a threshold value ($TH_{Fil}$);
- compare the value ($R_{Fil}$) to the determined threshold value ($TH_{Fil}$); and
- outputting an feature decision based on the comparison.

5. The system of claim 1 wherein the captured signals are further processed by estimating the frequency of the interference.

6. The system of claim 5 wherein the estimated frequency of the interference is utilized in the application of the comb filter.

7. The system of claim 5 wherein the estimated frequency of the interference is utilized in the estimate of the amplitude and phase.

8. The system of claim 1 wherein the output device provides at least one of a screen display and printed copy of the ECG.

9. A method for use in an ECG, the method comprising:
- applying a comb filter to a received signal to emphasize interference at a plurality of selected frequencies;
- estimating an amplitude and a phase of the applied filtered signal;
- performing a first stage of filtering on the applied filtered signals to remove power line interference using feature detection;
- performing a second stage of processing to the applied filtered signals to determine if the performed first stage misclassified a feature to further remove interference using feature detection, the second stage including estimating the interference level to determine if interference is low level or high level;
- estimating interference using the feature detection, amplitude and phase of the signal; and
- removing the estimated interference from the signal to generate a signal substantially free of power line interference.

10. The method of claim 9 wherein the first stage comprises:
- determining a value (R) from a ratio of a peak amplitude ($A_{peak}$) and a root-mean-square of the amplitudes of the interference harmonics ($A_{rms}$);
- calculating a running a histogram of the determined values (R) to calculate a cumulative distribution function (CDF) to determine a threshold value ($TH_R$);
- comparing the determined value (R) to the determined threshold value ($TH_R$); and
- outputting a feature decision based on the comparison.

11. The method of claim 9 further comprising, on a condition that there is low level interference in the estimate:
- determine a root-mean-square of the amplitudes of the interference harmonics ($A_{rms}$);
- calculate a running histogram of the determined root-mean-square of the amplitude ($A_{rms}$) to calculate a cumulative distribution function (CDF) to determine a threshold value ($TH_{rms}$);
- compare the root-mean-square of the amplitude ($A_{rms}$) to the determined threshold value ($TH_{rms}$); and
- outputting an feature decision based on the comparison.

12. The method of claim 9 further comprising, on a condition that there is high level interference in the estimate:
- determine a value ($R_{Fil}$) from a ratio of (first stage) filtered signal peak amplitude ($A_{Filpeak}$) and a root-mean-square of the amplitude ($A_{rms}$);
- calculate a running histogram of the values ($R_{Fil}$) to calculate a cumulative distribution function (CDF) to determine a threshold value ($TH_{Fil}$);
- compare the value ($R_{Fil}$) to the determined threshold value ($TH_{Fil}$); and
- outputting an feature decision based on the comparison.

13. A device for performing an electrocardiograph (ECG), the system comprising:
- a signal processor to process captured electrical signals from a plurality of leads configured to be attached to a subject by:
  - applying a comb filter to the captured electrical signals to emphasize interference at a plurality of selected frequencies;
  - estimating an amplitude and a phase of the applied filtered signals;

performing a first stage of filtering the applied filtered signals to remove power line interference using feature detection;

performing a second stage of filtering the applied filtered signals to remove power line interference using feature detection, the second stage including estimating the interference level to determine if interference is low level or high level;

estimating interference using the feature detection, amplitude and phase; and removing the estimated interference from the signal to generate a signal substantially free of power line interference.

14. The device of claim 13 further comprising, on a condition that there is high level interference in the estimate:

determine a first value ($R_{Fil}$) from a ratio of (first stage) filtered signal peak amplitude ($A_{Filpeak}$) and a root-mean-square of the amplitude ($A_{rms}$);

calculate a running histogram of the values ($R_{Fil}$) to determine a threshold value ($TH_{Fil}$);

compare the value ($R_{Fil}$) to the determined threshold value ($TH_{Fil}$); and outputting an feature decision based on the comparison.

15. The method of claim 9 further comprising estimating the frequency of the interference.

16. The method of claim 15 wherein the estimated frequency of the interference is utilized in the application of the comb filter.

17. The method of claim 15 wherein the estimated frequency of the interference is utilized in the estimate of the amplitude and phase.

18. The device of claim 13 further comprising, on a condition that there is low level interference in the estimate:

determine a root-mean-square of the amplitudes of the interference harmonics ($A_{rms}$);

calculate a running histogram of the determined root-mean-square of the amplitude ($A_{rms}$) to determine a threshold value ($TH_{rms}$);

compare the root-mean-square of the amplitude ($A_{rms}$) to the determined threshold value ($TH_{rms}$); and outputting a feature decision based on the comparison.

19. The device of claim 13 further comprising estimating the frequency of the interference, wherein the estimated frequency of the interference is utilized in the application of the comb filter.

20. The device of claim 13 further comprising estimating the frequency of the interference, wherein the estimated frequency of the interference is utilized in the estimate of the amplitude and phase.

* * * * *